(12) United States Patent
Straub et al.

(10) Patent No.: US 7,842,925 B2
(45) Date of Patent: Nov. 30, 2010

(54) RADIATION SOURCE FOR A SENSOR ARRANGEMENT WITH MAKING CURRENT LIMITATION

(75) Inventors: Kuno Straub, Freising (DE); Thomas Tille, München (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 688 days.

(21) Appl. No.: 11/670,561

(22) Filed: Feb. 2, 2007

(65) Prior Publication Data
US 2007/0181812 A1 Aug. 9, 2007

(30) Foreign Application Priority Data
Feb. 6, 2006 (DE) .................. 10 2006 005 310

(51) Int. Cl.
*G01J 5/02* (2006.01)
(52) U.S. Cl. .................................. 250/343
(58) Field of Classification Search .......... 240/343
See application file for complete search history.

(56) References Cited

U.S. PATENT DOCUMENTS

| 4,437,005 | A | * | 3/1984 | Ophoff et al. ............... 250/343 |
| 5,374,887 | A | | 12/1994 | Drobnik |
| 5,432,408 | A | * | 7/1995 | Matsuda et al. ......... 315/200 R |
| 7,507,967 | B2 | * | 3/2009 | Uchida et al. ............... 250/343 |
| 2002/0093293 | A1 | | 7/2002 | Mayama |
| 2003/0107357 | A1 | | 6/2003 | Uchikura et al. |
| 2003/0136911 | A1 | | 7/2003 | Martin |
| 2005/0088157 | A1 | | 4/2005 | Benzinger et al. |
| 2005/0247878 | A1 | * | 11/2005 | Baschant et al. ............. 250/343 |

FOREIGN PATENT DOCUMENTS

| DE | 10253980 A1 | 6/2004 |
| DE | 102004007946 A1 | 9/2005 |
| DE | 102004028077 A1 | 12/2005 |

OTHER PUBLICATIONS

Munteanu et al., "Portable rangefinder laser transmitter," 2003, SPIE Proceedings, vol. 5227, pp. 443-446.*
Valentine, Richard; Don't underestimate transistor-based lamp-driver design; EDN Jun. 7, 1990; pp. 119-124; No. 12; Newton, MA, US.

* cited by examiner

*Primary Examiner*—David P Porta
*Assistant Examiner*—Kiho Kim
(74) *Attorney, Agent, or Firm*—Barley Snyder LLC

(57) ABSTRACT

A radiation source for an optical sensor arrangement has an incandescent lamp being switched by a semiconductor switch. The incandescent lamp emits a broadband light spectrum. The semiconductor switch has a control terminal driven by a control signal to switch a connection of the incandescent lamp to a supply voltage. The semiconductor switch has a first terminal which is connected to the incandescent lamp, and a second terminal which is connected to a reference potential. When the semiconductor switch is in an on state, a current path is formed between the first and second terminals. A capacitor is connected between the control terminal and the first terminal. A first resistor connects the control terminal to the control signal and a second resistor or capacitor connects the control terminal to the reference potential.

14 Claims, 3 Drawing Sheets

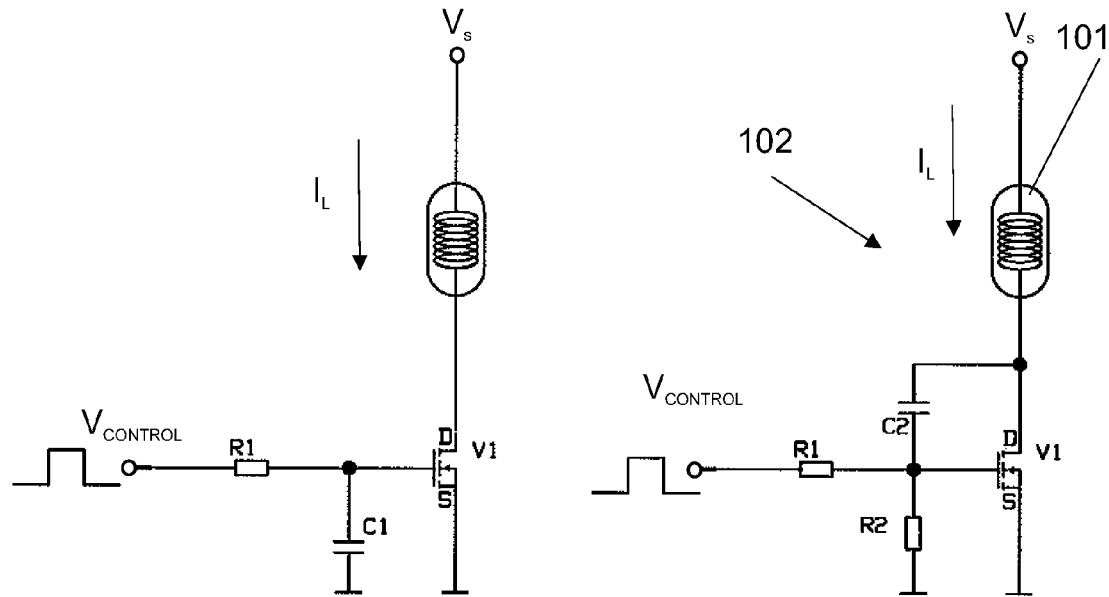
FIG. 1
*(Prior Art)*
FIG. 2
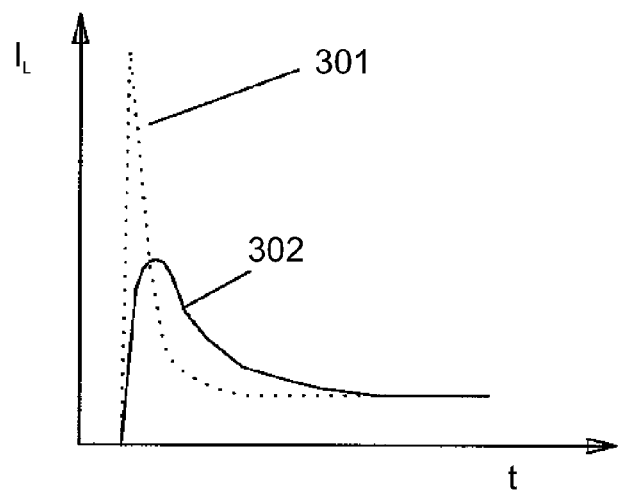
FIG. 3

RADIATION SOURCE FOR A SENSOR ARRANGEMENT WITH MAKING CURRENT LIMITATION

CROSS-REFERENCE TO RELATED APPLICATIONS

This application claims the benefit of the filing date under 35 U.S.C. §119(a)-(d) of German Patent No. DE 10 2006 005 310.4, filed Feb. 6, 2006.

FIELD OF THE INVENTION

The invention is related to a radiation source for an optical sensor arrangement and to a corresponding optical sensor arrangement. In particular, it relates to gas sensor arrangements which can be used in optical gas sensors, for example to detect $CO_2$.

BACKGROUND

In general, optical sensor arrangements are based on the principle that the radiation which is emitted by a radiation source passes through a measured distance, in which the analyte to be detected is present, and the change which occurs in the radiation intensity because of the presence of the analyte is evaluated by means of a corresponding detector. The radiation intensity can be affected by absorption, scattering or turbidity, and the analyte can be present in the liquid or gaseous phase.

Known gas sensor arrangements are used to detect the most diverse analytes, such as methane or carbon dioxide. They are based on the property of many polyatomic gases, that they absorb radiation, particularly in the infrared wavelength range. This absorption occurs at a wavelength which is characteristic of the relevant gas, for example for $CO_2$ at 4.24 μm. Using infrared gas sensors, it is therefore possible to establish the presence of a gas analyte and/or the concentration of this gas analyte in a gas to be measured.

Known gas sensor arrangements, such as are disclosed, for instance, in DE 10 2004 028077 A1 or DE 10 2004 007 946 A1, have a radiation source, an absorption distance, for example, a measurement space, and a radiation detector. According to the known Lambert-Beer law, the radiation intensity which the radiation detector measures is a measurement of the concentration of the absorbing gas. In the case of these so-called NDIR (non dispersive infrared) sensors, a broadband radiation source is used, and the relevant wavelength can be set via an interference filter or grating.

Carbon dioxide detection in particular is gaining increasing significance today in many application areas. For instance, the quality of the internal air can be monitored, the cleaning cycle of self-cleaning ovens can be monitored, and the supply of $CO_2$ to plants in greenhouses can be regulated. In the medical field, for example in anesthesia, the air of a patient's breath can be monitored, and finally, wherever the danger of escaping $CO_2$ exists, for instance in correspondingly filled air-conditioning systems, a carbon dioxide sensor can be used in a warning system.

In the motor vehicle field, carbon dioxide detection can be used to increase the energy efficiency of heating and air-conditioning, to monitor the $CO_2$ content of the interior air, to cause a fresh air supply by controlling an appropriate fan flap only if necessary, for example, in the case of increased $CO_2$ concentration.

Also, modern motor vehicle air-conditioning systems are based on $CO_2$ as the coolant, so that $CO_2$ gas sensors can monitor escaping $CO_2$ to detect leaks/defects. Particularly in the motor vehicle field, such gas sensor arrangements must meet the highest requirements for robustness, reliability, miniaturizability, and long life cycles.

In the case of known gas sensor arrangements, such as arrangements which are disclosed in DE 10 2004 028 077 A1, the radiation source is not usually operated uniformly, but pulsed at a specified frequency. For example, the radiation source, which is usually in the form of a miniature incandescent lamp, is operated by direct current (DC) which is switched by rectangular pulses.

It has been shown that the lamps which are switched on and off, again and again, are exposed to increased stress because of the making current which occurs each time, and thus have a shorter lifetime. To extend the lifetime of such incandescent lamps, which are switched on in pulsed operation, and in particular to reduce the high making current peaks, a known method is to switch the lamp on by a semiconductor, and to provide an RC element in the control circuit, to make it possible to switch the lamp on smoothly.

Such a known radiation source is shown schematically in FIG. 1. However, at the time of switching on there is always an overcurrent at a multiple, usually five to ten times, of the nominal current. This is shown in FIG. 3, in which the lamp current upon switching on is shown over time, as curve 301.

The cause of this high peak current can be seen in that the incandescent lamp filament in the cold operating state of the lamp has a significantly lower electrical resistance than in the hot operating state. It is only after a few milliseconds of operation that the incandescent filament reaches its operating temperature and thus its final electrical resistance, and the current through the lamp approaches the operating current value.

It is therefore desirable to reduce the stress on a radiation source for an optical sensor arrangement in pulsed operation, and thus to increase its lifetime, without excessively increasing the size and production costs.

SUMMARY

A radiation source is provided for an optical sensor arrangement having an incandescent lamp being switched by a semiconductor switch. The incandescent lamp emits a broadband light spectrum. The semiconductor switch has a control terminal driven by a control signal to switch a connection of the incandescent lamp to a supply voltage. The semiconductor switch has a first terminal which is connected to the incandescent lamp, and a second terminal which is connected to a reference potential. When the semiconductor switch is in an on state, a current path is formed between the first and second terminals. A capacitor is connected between the control terminal and the first terminal. A first resistor connects the control terminal to the control signal and a second resistor or capacitor connects the control terminal to the reference potential.

BRIEF DESCRIPTION OF THE DRAWINGS

The invention will now be described by way of example with reference to the accompanying figures of which:

FIG. 1 shows a radiation source with RC circuit according to the prior art;

FIG. 2 shows a radiation source with a circuit according to the invention to reduce the peak current;

FIG. 3 is a time representation of the making currents through the incandescent lamp for the circuits according to FIGS. 1 and 2;

DETAILED DESCRIPTION OF THE EMBODIMENT(S)

FIG. 2 shows a radiation source 102 according to the invention, for use in a so-called NDIR (non dispersive infrared) sensor. Here, a miniature incandescent lamp 101 is an the infrared source. This incandescent lamp 101 is connected by a first terminal to a supply voltage $V_S$, for example, a DC voltage, and by its second terminal, via a semiconductor switch V1, here, for example, an n-channel enhancement MOSFET, to ground. The semiconductor switch V1 is switched on and off at its gate terminal by a pulsed control signal $V_{CONTROL}$.

A single pulse, for which the HIGH level corresponds to a switched-on state of the lamp, is shown schematically at the input. In this way, the incandescent lamp 101 can be controlled by switching the semiconductor switch V1 on and off so that it emits light pulses.

Figure 4:
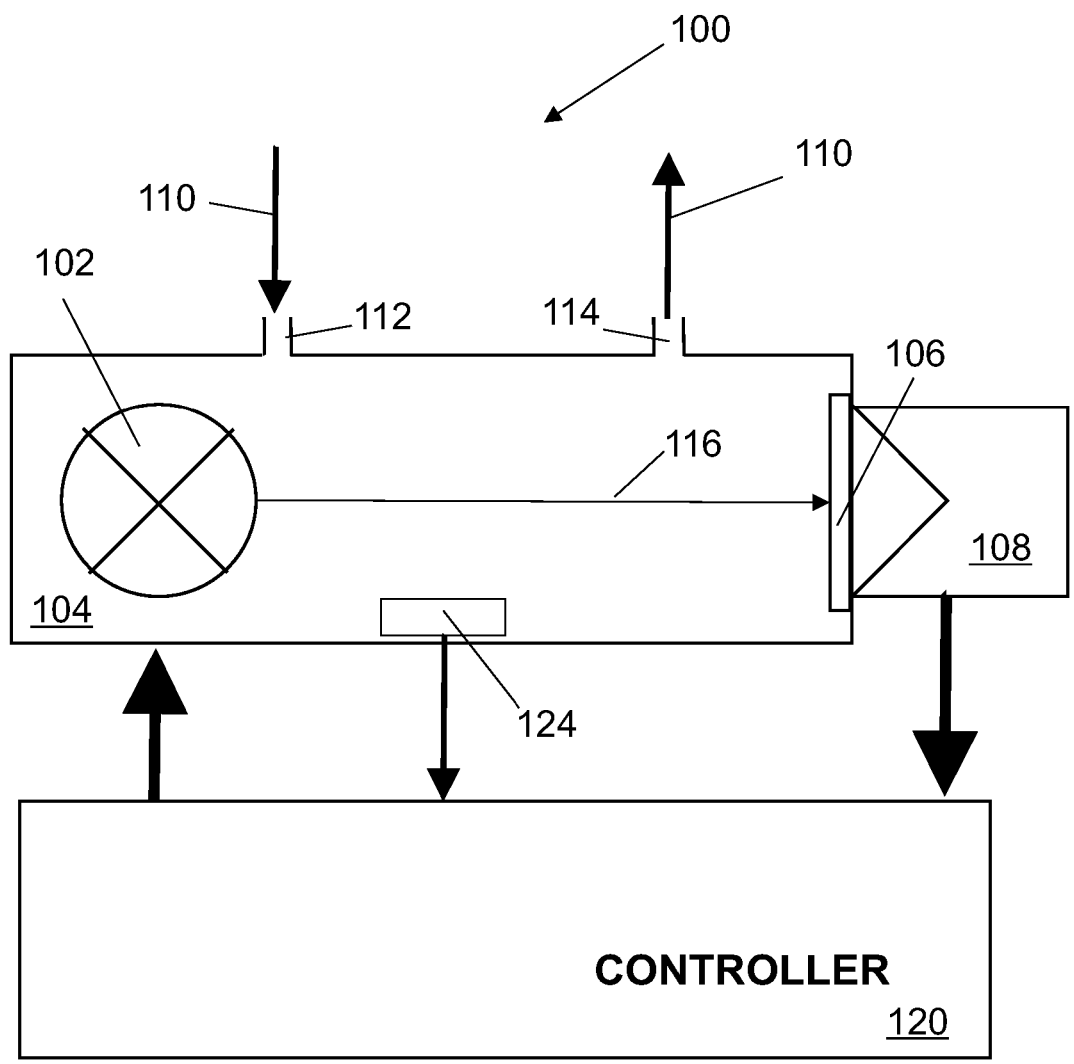
FIG. 4 is a block diagram of an optical sensor arrangement according to the invention and a first embodiment.

The radiation source 102 according to the invention forms the infrared source of a gas sensor unit 100, as shown in FIG. 4. The basic components here, apart from the infrared source 102, are the gas measurement space 104, a wavelength filter 106 and an infrared detector 108. However, the principles according to the invention can be used in the general sensor field, with all optical methods in which the turbidity or absorption is measured.

The measurement gas 110 is pumped or diffused into the gas measurement space 104, through the inlets and outlets 112, 114. The gas concentration can be determined electro-optically via the absorption of a particular wavelength in the infrared range. The emitted infrared radiation 116 is guided through the gas measurement space 104 to the detector 108. The detector 108 has an optical filter 106, which lets through only the wavelength range in which the gas molecules to be detected absorb. Other gas molecules normally absorb no light at this wavelength, and therefore do not affect the amount of radiation which reaches the detector 108. The IR signal is pulsed by the radiation source 102 by driving the semiconductor switch V1 appropriately, to be able to filter thermal background signals out of the desired signal. A controller 120 drives the radiation source 102 on the one hand, and on the other hand receives the output signals of the detector 108 and processes them further. A temperature sensor 124 can also be provided, to capture the temperature in the gas measurement space 104.

With reference to FIG. 2, the circuit according to the invention of the semiconductor switch V1 which in this case is a MOSFET and includes a capacitor C2, is connected by one terminal to the drain terminal of the MOSFET, and by its second terminal to the gate terminal of the MOSFET. A first resistor R1 is connected on the one hand to the control terminal of the MOSFET and on the other hand to the control signal $V_{CONTROL}$ to control the lamp. A second resistor R2 is provided between the gate terminal of the MOSFET and ground. Alternatively, the second resistor R2 can be replaced by a capacitor (not shown here).

The advantages of this circuit according to the invention to reduce peak currents, also called "inrush currents", can be seen from the representation in FIG. 3.

FIG. 3 shows the lamp current $I_L$ through the incandescent lamp 101 over time when the semiconductor switch V1 is switched on, i.e. when a rising pulse occurs on the control signal $V_{CONTROL}$. The curve 302 shows lamp current in the circuit according to FIG. 2, in comparison with a current curve 301 when the semiconductor switch is connected according to the arrangement of FIG. 1.

It can clearly be seen that by increasing the Miller capacitance of the semiconductor switch V1 by means of the capacitor C2, the switching performance of the semiconductor switch V1 is changed so that the peak making current is significantly reduced. Although in the circuit according to the invention, the lamp current $I_L$ does not reach its final value until later than in the case of the known circuit according to FIG. 1, this is not a problem with comparatively low switching frequencies. The lamp stress which occurs particularly in the case of frequent on and off switching cycles because of increased peak currents can be significantly improved by the circuit according to the invention.

Figure 5:
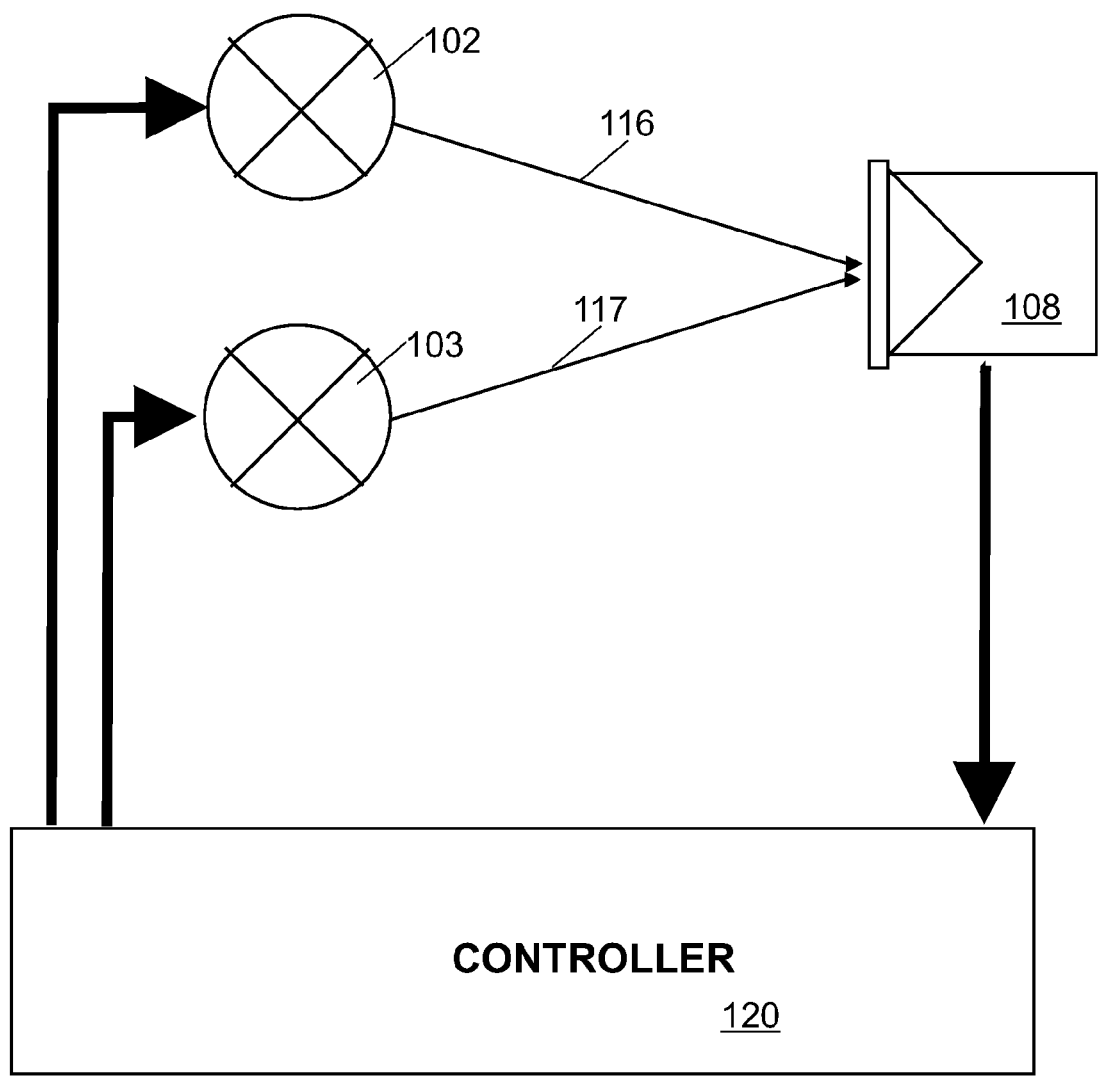
FIG. 5 is a block diagram of an optical sensor arrangement according to the invention and another embodiment.

The principles according to the invention can also be used if, instead of a single infrared radiation source 102, two radiation sources 102, 103 are provided, as shown in FIG. 5. In this case, radiation source 102 may be utilized as a measurement source while and at least one reference radiation source 103 is provided. Radiation source 103 is arranged symmetrically to at least one axis of symmetry of the measurement space 104 and the detector 108 is arranged on this axis of symmetry so that the beam paths of the radiation sources 102, 103 have the same effective path length to the detector 108.

Since the incandescent lamp 101 is, for instance, a miniature incandescent lamp which is operated at around 6 V and at very low power ranges, the components R1, R2 and C2 can be implemented as thick film resistors according to industry standard format 0603, or the capacitor can be implemented as a ceramic multi-layer chip capacitor according to industry standard format 0603 or 0805. In this way, the whole circuit can be miniaturized to a very large extent. The semiconductor switch V1 can be provided as a SOT 23, for instance.

Advantageously, the lifetime of lamps 101 which are used as a radiation source 102, 103 in a gas sensor is considerably extended, particularly in the case of applications with pulsing lamp operation. Additionally, the peak current consumption of the application can be notably reduced, for which reason smaller components also can be used in some circumstances.

Advantageously, the peak currents which occur are no longer effective as sources of interference. This is particularly important in the motor vehicle field, for smooth running of electronic control processes.

The embodiments shown provide especially efficient reduction of the peak currents which occur if the semiconductor switch V1 is a MOSFET. For instance, an n-channel enhancement FET could be used here. In the case of a MOSFET as the semiconductor switch V1, the so-called Miller capacitance which is present in any case between the gate and the drain, and which the component manufacturers usually keep as low as possible to speed up the switching performance, is amplified by the external circuit, and the switching performance of the MOSFET is thus slowed down directly, to keep the peak currents which occur at switching on as low as possible.

Because the switching performance of the semiconductor switch V1 is slowed down by the circuit according to the invention, the arrangement can be used most effectively if a DC voltage supply is used. In this case, the reference potential can be an ground potential.

Also, since energy is converted into power loss by the recharging of the capacitance between the control terminal and the first terminal and also by the resistor circuit, the circuit according to the invention can be used especially advantageously with a miniature incandescent lamp 101 with a maximum power consumption of 0.5 W to 5.0 W. Higher powers are possible in principle, but they necessitate actions to avoid damage by the power losses which occur.

The advantageous properties of the optical sensor arrangement according to the invention can be used, in particular, for detection of carbon dioxide, for example in the motor vehicle field, both for monitoring $CO_2$ escaping from leaks and for checking the air quality in the passenger internal space. Obviously, however, the sensor arrangement according to the invention can also be used to detect other gases, to measure turbidity or similarly in liquids.

The ideas of this invention can also be transferred to the field of use of a sensor arrangement in which a measurement radiation source 102 and a reference radiation source 103 are compared with each other during a referencing phase. In this application case, the lifetime of both the measurement radiation source and the reference radiation source can be advantageously increased by driving them according to the invention. An example of such radiation source is shown in German patent specification DE 199 25 196 C2. There, the reference radiation source 103 is not used for normal measurement, but is operated at large monitoring intervals to determine the aging of the measurement radiation source. This operation of the reference radiation source 103 at large time intervals and for only short duration is so that the aging of the reference radiation source can be neglected compared with the aging of the measurement radiation source 102.

What is claimed is:

1. A radiation source for an optical sensor arrangement comprising:
    an incandescent lamp (101),
    a semiconductor switch (V1) switching a connection of the incandescent lamp (101) to a supply voltage ($V_s$), said switch having a first terminal which is connected to the incandescent lamp (101), and a second terminal which is connected to a reference potential, wherein in the switched-on state of the semiconductor switch (V1) a current path is formed between the first and second terminals, and wherein the semiconductor switch (V1) has a control terminal to apply a control signal ($V_{CONTROL}$),
    a capacitor (C2) connected between the control terminal and the first terminal,
    a first resistor (R1), connecting the control terminal to the control signal and
    a second resistor (R2) or capacitor connecting the control terminal to the reference potential.

2. The radiation source according to claim 1, wherein the semiconductor switch (V1) is a MOSFET, wherein the first terminal is a drain terminal and the second terminal is a source terminal, and wherein the control terminal is a gate terminal of the MOSFET.

3. The radiation source according to claim 2, wherein the supply voltage ($V_s$) is a DC voltage.

4. The radiation source according to claim 1, wherein the reference potential is ground potential.

5. The radiation source according to claim 1, wherein the incandescent lamp (101) is a miniature incandescent lamp with a power consumption of 0.5 W to 5.0 W.

6. An optical sensor arrangement comprising:
    at least one radiation-emitting radiation source (102, 103),
    a measurement space (104), which can be filled with a fluid (110) containing at least one analyte to be measured,
    at least one detector (108) which detects the radiation and generates an output signal depending on the presence and/or concentration of the analyte,
    an incandescent lamp (101) of the radiation source,
    a semiconductor switch (V1) of the radiation source to switch a connection of the incandescent lamp (101) to a supply voltage ($V_s$), said switch having a first terminal which is connected to the incandescent lamp (101), and a second terminal which is connected to a reference potential, wherein in the switched-on state of the semiconductor switch (V1) a current path is formed between the first and second terminals, and wherein the semiconductor switch (V1) has a control terminal to apply a control signal ($V_{CONTROL}$),
    a capacitor (C2) connected between the control terminal and the first terminal,
    a first resistor (R1), connecting the control terminal to the control signal and
    a second resistor (R2) or capacitor connecting the control terminal to the reference potential.

7. The sensor arrangement according to claim 6, wherein the semiconductor switch (V1) is a MOSFET, wherein the first terminal is a drain terminal and the second terminal is a source terminal, and wherein the control terminal is a gate terminal of the MOSFET.

8. The sensor arrangement according to claim 7 wherein the supply voltage ($V_s$) is a DC voltage.

9. The sensor arrangement according to claim 6 wherein the reference potential is ground potential.

10. The sensor arrangement according to claim 6, wherein the incandescent lamp (101) is a miniature incandescent lamp with a power consumption of 0.5 W to 5.0 W.

11. The sensor arrangement according to claim 6 wherein the control signal ($V_{CONTROL}$) is a pulsed signal, to operate the incandescent lamp (101) so that it emits light pulses defined by the control signal.

12. The sensor arrangement according to claim 6 wherein the radiation to be detected is infrared radiation.

13. The sensor arrangement according to claim 6 wherein at least one measurement radiation source (102) and at least one reference radiation source (103) are provided, and are arranged symmetrically to at least one axis of symmetry of the measurement space (104), and wherein the detector device (108) is arranged on this axis of symmetry so that the beam paths of the radiation sources have the same effective path length to the detector device.

14. The sensor arrangement according to claim 6 wherein the analyte is carbon dioxide.

* * * * *